(12) United States Patent
Gilbert

(10) Patent No.: US 8,968,293 B2
(45) Date of Patent: Mar. 3, 2015

(54) SYSTEMS AND METHODS FOR CALIBRATING POWER MEASUREMENTS IN AN ELECTROSURGICAL GENERATOR

(75) Inventor: James A. Gilbert, Boulder, CO (US)

(73) Assignee: Covidien LP, Mansfield, MA (US)

(*) Notice: Subject to any disclaimer, the term of this patent is extended or adjusted under 35 U.S.C. 154(b) by 865 days.

(21) Appl. No.: 13/085,278

(22) Filed: Apr. 12, 2011

(65) Prior Publication Data

US 2012/0265195 A1     Oct. 18, 2012

(51) Int. Cl.
| | | |
|---|---|---|
| *A61B 18/12* | (2006.01) | |
| *H03H 21/00* | (2006.01) | |
| *H03H 17/00* | (2006.01) | |
| *H03H 17/02* | (2006.01) | |
| *A61B 18/14* | (2006.01) | |
| *H03H 17/04* | (2006.01) | |
| *A61B 18/00* | (2006.01) | |

(52) U.S. Cl.
CPC ........ *H03H 21/0012* (2013.01); *A61B 18/1233* (2013.01); *A61B 18/1445* (2013.01); *H03H 17/0027* (2013.01); *H03H 17/0251* (2013.01); *H03H 17/0283* (2013.01); *H03H 2017/0472* (2013.01); *A61B 18/1206* (2013.01); *A61B 2018/00648* (2013.01); *A61B 2018/00702* (2013.01); *A61B 2018/00827* (2013.01); *A61B 2018/00892* (2013.01)
USPC .......................................................... 606/34

(58) Field of Classification Search
USPC ........................................ 606/34, 33, 38, 41
See application file for complete search history.

(56) References Cited

U.S. PATENT DOCUMENTS

| | | |
|---|---|---|
| 5,743,900 A | 4/1998 | Hara |
| 5,931,835 A | 8/1999 | Mackey |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

Tryoa Chincilla, A.L. Synchronization and Channel Estimation in OFDM: Algorithms for Efficient Implementation of WLAN Systems. (2004). Dissertation.*

(Continued)

*Primary Examiner* — Joseph Stoklosa
*Assistant Examiner* — Eunhwa Kim

(57) ABSTRACT

The disclosed electrosurgical systems and methods accurately determine the power actually applied to a load by using equalizers to calibrate the power measurements. The electrosurgical systems include an electro surgical generator and an electrosurgical instrument coupled to the electrosurgical generator through an electrosurgical cable. The electrosurgical generator includes an electrical energy source, voltage and current detectors, equalizers that estimate the voltage and current applied to a load, and a power calculation unit that calculates estimated power based upon the estimated voltage and current. The methods of calibrating an electro surgical generator involve applying a resistive element across output terminals of the electrosurgical generator, applying a test signal to the resistive element, measuring the magnitude and phase angle of voltage and current components of the test signal within the electrosurgical generator, estimating the magnitude and phase angle of the voltage and current at the resistive element using equalizers, and determining gain correction factors and minimum phase angles for the equalizers.

6 Claims, 7 Drawing Sheets

(56) References Cited

U.S. PATENT DOCUMENTS

| | | | |
|---|---|---|---|
| 5,931,836 | A | 8/1999 | Hatta et al. |
| 6,508,815 | B1 | 1/2003 | Strul et al. |
| 7,300,435 | B2 * | 11/2007 | Wham et al. .................. 606/34 |
| D574,323 | S | 8/2008 | Waaler |
| 7,407,502 | B2 | 8/2008 | Strul et al. |
| 7,766,905 | B2 | 8/2010 | Paterson et al. |
| 2005/0113819 | A1 | 5/2005 | Wham et al. |
| 2005/0182398 | A1 | 8/2005 | Paterson |
| 2006/0232471 | A1 * | 10/2006 | Coumou ....................... 342/450 |
| 2007/0112532 | A1 * | 5/2007 | Pupalaikis ..................... 702/79 |
| 2009/0112204 | A1 | 4/2009 | Aronow et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1157667 | 11/2001 |
| EP | 1157667 A2 | 11/2001 |
| EP | 1366724 | 1/2006 |
| EP | 880220 | 6/2006 |
| EP | 1776929 | 4/2007 |
| EP | 2301463 | 3/2011 |
| EP | 2301463 A1 | 3/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

Sac. M., Blok, M. Gain deficit effect in the fractional delay filter design by the window method. (2009). Photonics Applications in Astronomy, Communications, Industry, and High-Energy Physics Experiments. vol. 7502, doi: 10.1117/12.75021.*
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnson.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12. 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.

(56) References Cited

OTHER PUBLICATIONS

Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
European Search Report for European Application No. 12163969.4 dated Jul. 16, 2012.
U. Zolzer, "Equalizers", Digital Audio Signal Processing, John Wiley and Sons, 1997, 19 pp.
B. Widrow and S. Stearns, "Inverse Adaptive Modeling, Equalization, and Deconvolution," Prentice-Hall, 1985, 6 pp.
A. Williams and F. Taylor, "Networks for the Time Domain", Electronic Filter Design Handbook: LC, Active, and Digital Filters, 2nd Edition, McGraw-Hill, 1988, 4 pp.
European Search Report dated Aug. 29, 2014, in corresponding EP Application No. 14169809.2.

* cited by examiner

SYSTEMS AND METHODS FOR CALIBRATING POWER MEASUREMENTS IN AN ELECTROSURGICAL GENERATOR

BACKGROUND

1. Technical Field

The present disclosure generally relates to electrosurgery. More particularly, the present disclosure relates to systems and methods for calibrating power measurements within an electrosurgical generator.

2. Background of Related Art

Electrosurgery involves the application of high-frequency electric current to cut or modify biological tissue during a surgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz to avoid muscle and/or nerve stimulation.

During electrosurgery, the alternating current generated by the electrosurgical generator is conducted through tissue disposed between the active and return electrodes. The tissue's impedance converts the electrical energy (also referred to as electrosurgical energy) associated with the alternating current into heat, which causes the tissue temperature to rise. The electrosurgical generator controls the heating of the tissue, by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the electrosurgical instrument itself. In monopolar electrosurgery, the return electrode is part of a device usually referred to as a return pad.

An electrosurgical generator includes a controller that controls the power applied to a load, i.e., the tissue, over some period of time. The power applied to the load is controlled based upon the power determined at the output of the electrosurgical generator and a power level set by the user or a power level needed to achieve a desired tissue effect. The power at the output of the electrosurgical generator is determined by measuring the voltage and current at the output of the electrosurgical generator and calculating the average power based upon the measured voltage and current.

The voltage and current measured by the sensors at the output of the electrosurgical generator, however, may not equal the actual voltage and current applied to the load, i.e., the tissue, because of errors in the voltage and current measurements. These measurement errors may be caused by parasitics in the cable connecting the electrosurgical generator to the electrosurgical instrument, parasitics in the analog processing circuitry, and/or delays of the analog to digital conversion process. As a result, the power calculations may be inaccurate and may lead to improper control of the electrosurgical energy applied to the tissue.

SUMMARY

The system and method of the present disclosure accurately determines the power actually applied to tissue by calibrating the power measurements within an electrosurgical generator using equalizers at a desired frequency or over a narrow bandwidth of frequencies. The equalizers have low computational complexity and may be implemented using commonly available microprocessors, field programmable gate arrays (FPGAs), or digital signal processors (DSPs).

In one aspect, the present disclosure features an electrosurgical generator system. This system includes an electrosurgical generator and an electrosurgical instrument coupled to the electrosurgical generator through an electrosurgical cable. The electrosurgical instrument is configured to apply electrosurgical energy to body tissue. The electrosurgical generator includes an radio frequency (RF) electrical energy source, a voltage detector coupled to the RF electrical energy source, a current detector coupled to the RF electrical energy source, an equalizer unit configured to equalize the voltage detected by the voltage detector and the current detected by the current detector, and a power calculation unit that calculates power based upon the equalized voltage and current.

In some embodiments, the electrosurgical generator includes a digital signal processor (DSP), which includes the equalizer unit and the power calculation unit. The equalizer unit may include a Least Mean Squares (LMS) adaptive filter, a gain and a fractional delay line, at least one gain and an all-pass delay filter, or a bandpass parametric equalizer. The bandpass parametric equalizer may be a shelving boost filter, a shelving cut filter, or a peak filter. The equalizer unit may also include a polyphase filter and decimator configured to perform equalization, filtering, and decimation as a combined function.

In some embodiments, the electrosurgical generator system further includes analog-to-digital converters electrically coupled to the current and voltage detectors. The power calculation unit calculates actual power applied to the electrosurgical instrument.

The present disclosure, in another aspect, features a method of controlling an electrosurgical generator system. The method includes generating RF electrical energy, sensing the voltage and current of the RF electrical energy, equalizing the voltage and current of the RF electrical energy, calculating power based upon the equalized voltage and current, and modifying the power of the RF electrical energy based upon the calculated power to achieve desired tissue effects.

In some embodiments, equalizing the voltage and current of the RF electrical energy includes filtering the sensed voltage and the sensed current with an LMS adaptive filter. In other embodiments, equalizing the sensed voltage and the sensed current of the RF electrical energy includes applying a gain to the sensed voltage and the sensed current and delaying the result of applying a gain to the sensed voltage and the sensed current to correct unequal group delay. The delay may be a fractional delay line filter. In yet other embodiments, equalizing the sensed voltage and the sensed current of the RF electrical energy includes applying a gain to the sensed voltage and the sensed current and filtering the result with an all-pass delay filter. In yet other embodiments, equalizing the sensed voltage and the sensed current of the RF electrical energy includes equalizing the sensed voltage and the sensed current of the RF electrical energy using a bandpass parametric equalizer, such as a shelving boost filter, a shelving cut filter, or a peak filter.

In some embodiments, the method includes converting the sensed voltage and current to digital form. Also, calculating power based upon the equalized voltage and current includes calculating the actual average power applied to a load. In addition, modifying the power of the RF electrical energy includes comparing the calculated power to a preset power value or desired power value based on the calculated tissue impedance, and modifying the power of the electrosurgical energy based upon the result of comparing the calculated power to the preset power value or desired power value.

The present disclosure, in yet another aspect, features a method of calibrating power measurements in an electrosurgical generator. The method includes selecting a resistive element; applying the resistive element across the output terminals of the electrosurgical generator; generating a test signal at a desired frequency; applying the test signal to the resistive element; measuring first magnitude values and first phase angle values of voltage and current components of the test signal at the output terminals; estimating second magnitude values and second phase angle values for the voltage and current components of the test signal using a first equalizer for the voltage component and a second equalizer for the current component; determining gain correction factors for the first and second equalizers based on the measured and estimated magnitudes of the voltage and current components of the test signal; and determining the minimum phase angle of the first and second equalizers based on the measured and estimated phase angles of the voltage and current components of the test signal.

BRIEF DESCRIPTION OF THE DRAWINGS

Various embodiments of the present disclosure are described with reference to the accompanying drawings wherein.

DETAILED DESCRIPTION

Figure 1:
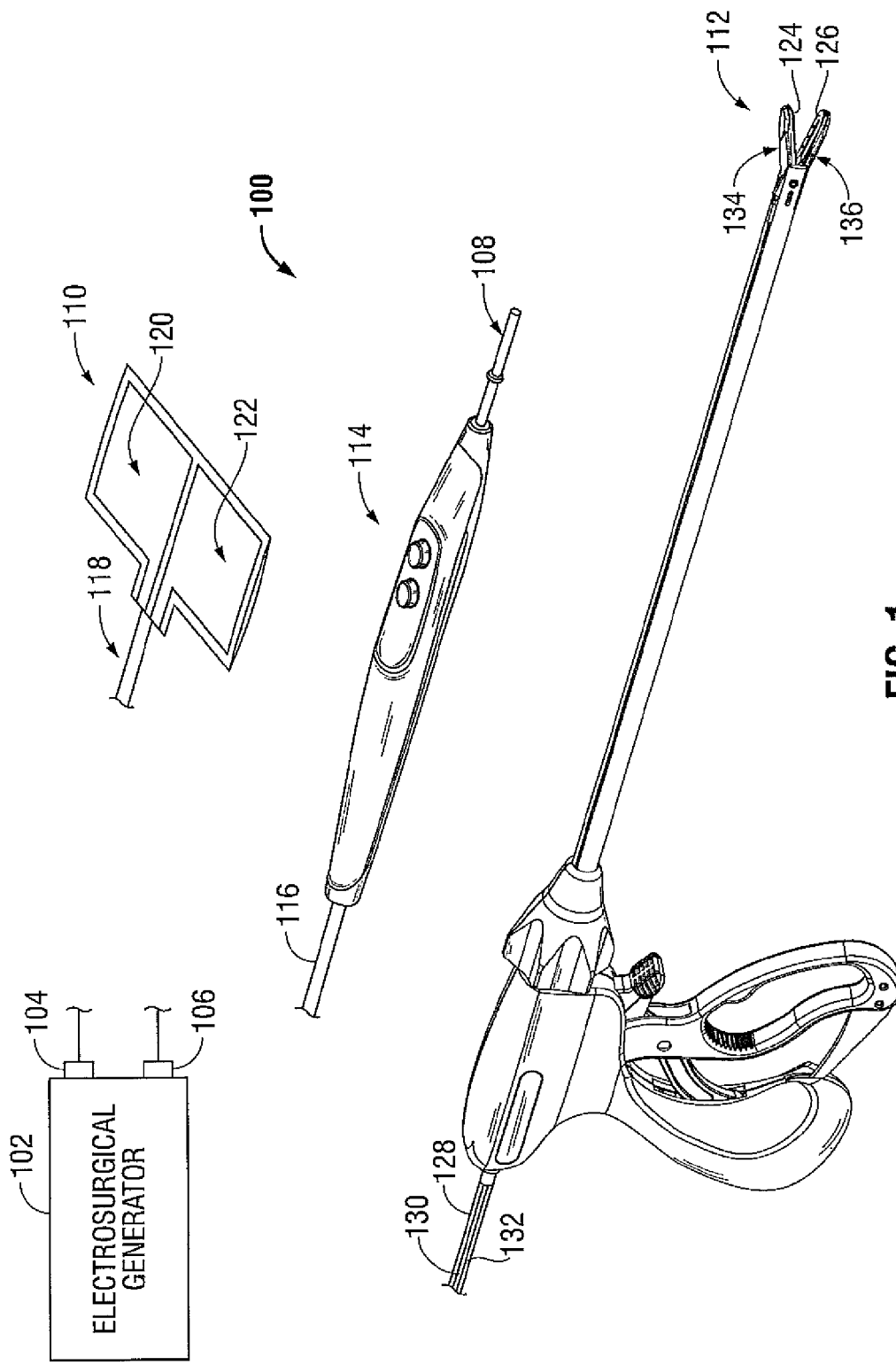
FIG. 1 is an illustration of an electrosurgical system in accordance with embodiments of the present disclosure.

FIG. 1 illustrates a bipolar and monopolar electrosurgical system 100 in accordance with embodiments of the present disclosure. The electrosurgical system 100 includes an electrosurgical generator 102 that measures and calculates the power delivered to a load through an electrosurgical instrument. The electrosurgical generator 102 performs monopolar and bipolar electrosurgical procedures, including vessel sealing procedures. The electrosurgical generator 102 may include a plurality of outputs (e.g., terminals 104 and 106) for interfacing with various electrosurgical instruments (e.g., a monopolar active electrode 108, a return pad 110, bipolar electrosurgical forceps 112, and a footswitch (not shown)). The electrosurgical generator 102 also includes electronic circuitry that generates radio frequency power for various electrosurgical modes (e.g., cutting, coagulating, or ablating) and procedures (e.g., monopolar, bipolar, or vessel sealing).

The electrosurgical system 100 includes a monopolar electrosurgical instrument 114 having one or more electrodes 108 for treating tissue of a patient (e.g., an electrosurgical cutting probe or ablation electrodes). Electrosurgical energy, e.g., radio frequency (RF) current, is supplied to the instrument 114 by the electrosurgical generator 102 via a supply line 116, which is connected to an active terminal 104 of the electrosurgical generator 102, allowing the instrument 114 to coagulate, seal, ablate and/or otherwise treat tissue. The electrosurgical current returns from the tissue via a return line 118 of the return pad 110 to a return terminal 106 of the electrosurgical generator 102. The active terminal 104 and the return terminal 106 may include connectors (not explicitly shown) configured to interface with plugs (also not explicitly shown) disposed at the end of the supply line 116 of the instrument 114 and at the end of the return line 118 of the return pad 110.

The electrosurgical system 100 includes return electrodes 120 and 122 within return pad 110 that are arranged to minimize the risk of tissue damage by maximizing the overall contact area with the patient's tissue. In addition, the electrosurgical generator 102 and the return pad 110 may be configured to monitor tissue-to-patient contact to insure that sufficient contact exists between the return pad 110 and the patient to minimize the risk of tissue damage.

The electrosurgical system 100 also includes a bipolar electrosurgical forceps instrument 112 having two or more electrodes (e.g., electrodes 124, 126) for treating tissue of a patient. The instrument 112 includes opposing jaw members 134, 136. The first jaw member 134 includes an active electrode 124 and the second jaw member 136 includes a return electrode 126. The active electrode 124 and the return electrode 126 are connectable to the electrosurgical generator 102 through cable 128, which includes a supply line 130 and a return line 132. The supply line 130 is connectable to the active terminal 104 and the return line 132 is connectable to the return terminal 106. The instrument 112 connects to the active terminal 104 and the return terminal 106 of the electrosurgical generator 102 through a plug (not explicitly shown) disposed at the end of the cable 128.

The electrosurgical generator 102 may be any suitable type of generator (e.g., electrosurgical or microwave) and may include a plurality of connectors to accommodate various types of electrosurgical instruments (e.g., instrument 114 and electrosurgical forceps 112). The electrosurgical generator 102 may also be configured to operate in a variety of modes, such as ablation, monopolar cutting, bipolar coagulation, and other modes. The electrosurgical generator 102 may include a switching mechanism (e.g., relays) to switch the supply of RF energy between the connectors. For example, when the instrument 114 is connected to the electrosurgical generator 102, the switching mechanism switches the supply of RF energy to only the monopolar plug. The active terminal 104 and the return terminal 106 may be coupled to a plurality of connectors (e.g., inputs and outputs) of the electrosurgical generator 102 to power a variety of instruments.

The electrosurgical generator 102 includes suitable input controls (e.g., buttons, activators, switches, or touch screens) for controlling the electrosurgical generator 102. In addition, the electrosurgical generator 102 may include one or more display screens for providing the user with a variety of output information (e.g., intensity settings and treatment complete indicators). The controls allow the user to adjust parameters of the RF electrical energy (e.g., the power or the waveform) so that they are suitable for a particular task (e.g., coagulating, tissue sealing, or cutting). The instruments 112 and 114 may also include a plurality of input controls that may be redundant with certain input controls of the electrosurgical generator 102. Placing the input controls at the instruments 112 and 114 allow for easier and faster modification of RF energy parameters during the surgical procedure without requiring interaction with the electrosurgical generator 102.

Figure 2:
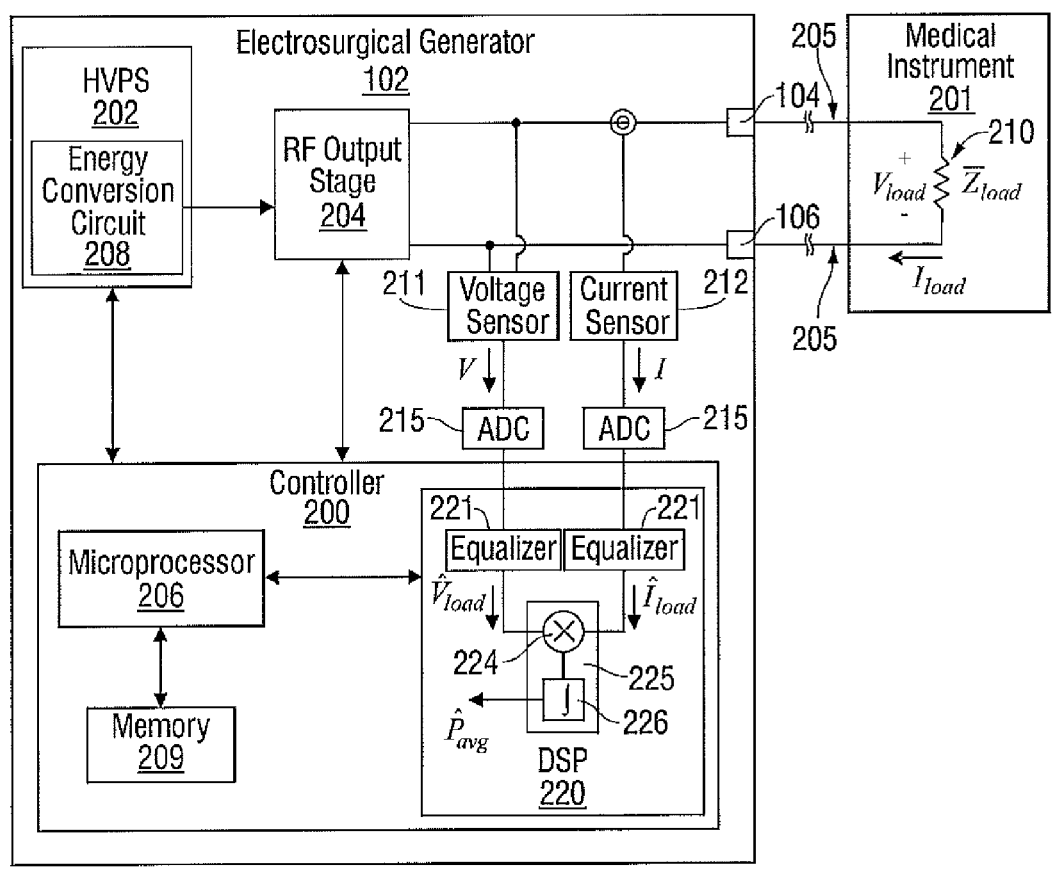
FIG. 2 is a block diagram of the electrosurgical generator of FIG. 1 coupled to a medical instrument in accordance with embodiments of the present disclosure.

FIG. 2 is a block diagram of the electrosurgical generator 102 of FIG. 1 and a corresponding medical instrument 201 in accordance with embodiments of the present disclosure. The electrosurgical generator 102 includes a controller 200, a high voltage power supply 202, and a radio frequency output stage 204. The controller 200 includes a microprocessor 206 and a memory 209. The microprocessor may be any suitable microcontroller, microprocessor (e.g., Harvard or Von Neumann architectures), PLD, PLA, or other suitable digital logic. Memory 209 may be volatile, non-volatile, solid state, magnetic, or other suitable storage memory.

Controller 200 may also include various circuitry (e.g., amplifiers or buffers) that serves as an interface between the microprocessor 206 and other circuitry within the electrosurgical generator 102. Controller 200 receives various feedback signals that are analyzed by the microprocessor 206 to provide control signals based on the feedback signals. The control signals from controller 200 control the HVPS 202 and the RF output stage 204 to provide electrosurgical energy to tissue, represented by a load 210 ($Z_{load}$).

The HVPS 202 includes an energy conversion circuit 208, which converts AC from an AC source or direct current (DC) from a DC source at a first energy level into DC at a second different energy level. The energy conversion circuit 208 supplies the DC power at the second different energy level to the RF output stage 204 based on control signals from the controller 200. The RF output stage 204 inverts the DC power output from the energy conversion circuit 208 to produce a high-frequency alternating current (e.g., RF AC), which is applied to the load 210. For example, the RF output stage 204 may generate a high-frequency alternating current using push-pull transistors coupled to a primary side of a step-up transformer (not shown).

The electrosurgical generator 102 and controller 200 include circuitry that determines and controls the power actually applied to the load 210 ($Z_{load}$). The average power at the load 210 may be calculated according to the equation:

$$P_{avg} = V_{rms} \cdot I_{rms} \cdot \cos \phi_{VI},$$

where $P_{avg}$ is the average power in watts, $V_{rms}$ is the root-mean-square value of the sinusoidal load voltage $V_{load}$, $I_{rms}$ is the root-mean-square value of the sinusoidal load current $I_{load}$, and $\phi_{VI}$ is the phase angle between the load voltage $V_{load}$ and the load current $I_{load}$.

Alternatively, the average power may be calculated according to the equation:

$$P_{avg} = \frac{1}{T} \int_{t_1-T}^{t_1} v(t) \cdot i(t) \, dt,$$

where T is the averaging time constant, v(t) is the load voltage as a function of time, and i(t) is the load current as a function of time. The controller 200 uses the calculated average power at the load as feedback to control the energy conversion circuit 208 so that the average power at the load is equal to a power level set by the user to achieve a desired tissue effect.

As shown in FIG. 2, electrosurgical generators typically include a voltage sensor 211 and a current sensor 212 coupled to the output of the RF output stage 204 to sense a voltage and a current for the average power calculations. The voltage sensor 211 measures the voltage across the output leads of the RF output stage 204 and provides an analog signal representing the measured voltage to an analog-to-digital converter ("ADC") 215. ADC 215 converts the analog signal to a digital signal. The current sensor 212 measures the current on the output lead of the RF output stage 204 that is connected to the output terminal 104 of the electrosurgical generator 102. The current sensor 212 provides an analog signal representing the measured current to an ADC 215, which converts the analog signal to a digital signal.

In some electrosurgical generators, the digital voltage and current signals are used to calculate the average power at the load. However, processing delays associated with the measurement circuitry (i.e., the sensors 211, 212 and ADCs 215) and electrical parasitic components in the cable 205 and in the measurement circuitry may introduce errors into the voltage and current measurements. Because of errors in the measurements, the magnitude of the measured voltage may not be equal to the magnitude of the voltage actually applied to the load 210, and/or the magnitude of the measured current may not be equal to the magnitude of the current actually applied to the load 210, and/or the phase difference between the measured voltage and current may not be equal to the phase difference between the voltage and current actually applied to the load 210. As a result, the average power calculated based on the magnitudes of the voltage and current and their phase difference may not be equal to the average power actually applied to the load 210.

The systems and methods according to embodiments of the present disclosure minimize these measurement errors by introducing equalizers to equalize the power measurements made in the electrosurgical generator 102 to the actual power applied to the load 210. As shown in FIG. 2, the electrosurgical generator 102 incorporates equalizers 221 (e.g., filters or algorithms). A first equalizer 221 is coupled in series with the voltage sensor 211 and a corresponding ADC 215 and a second equalizer 221 is coupled in series with the current sensor 212 and a corresponding ADC 215.

The equalizers 221 are implemented in a digital signal processor (DSP) 220 of the controller 200. The equalizers 221 receive measurements from the sensors 211, 212 and generate an estimated load voltage $\hat{V}_{load}$ and an estimated load current $\hat{I}_{load}$. The DSP 220 also implements an average estimated power calculator 225 that calculates the average estimated power at the load $\hat{P}_{avg}$ based on the estimated load voltage $\hat{V}_{load}$ and the estimated load current $\hat{I}_{load}$. The average estimated power calculator 225 includes a multiplier 224 that multiplies the estimated load voltage $\hat{V}_{load}$ by the estimated load current $\hat{I}_{load}$ and an integrator 226 that integrates the output from the multiplier 224 to obtain the average estimated power at the load $\hat{P}_{avg}$.

The DSP 220 communicates the calculated average estimated power at the load $\hat{P}_{avg}$ to the microprocessor 206, which uses the average estimated power at the load $\hat{P}_{avg}$ to control the energy conversion circuit 208. For example, the microprocessor 206 may execute a Proportional-Integral-Derivative (PID) control algorithm based on the average estimated power at the load $\hat{P}_{avg}$ and a desired power level, which may be selected by a user, to determine the amount of electric current that should be supplied by the energy conversion circuit 208 to achieve and maintain the desired power level.

Figure 3:
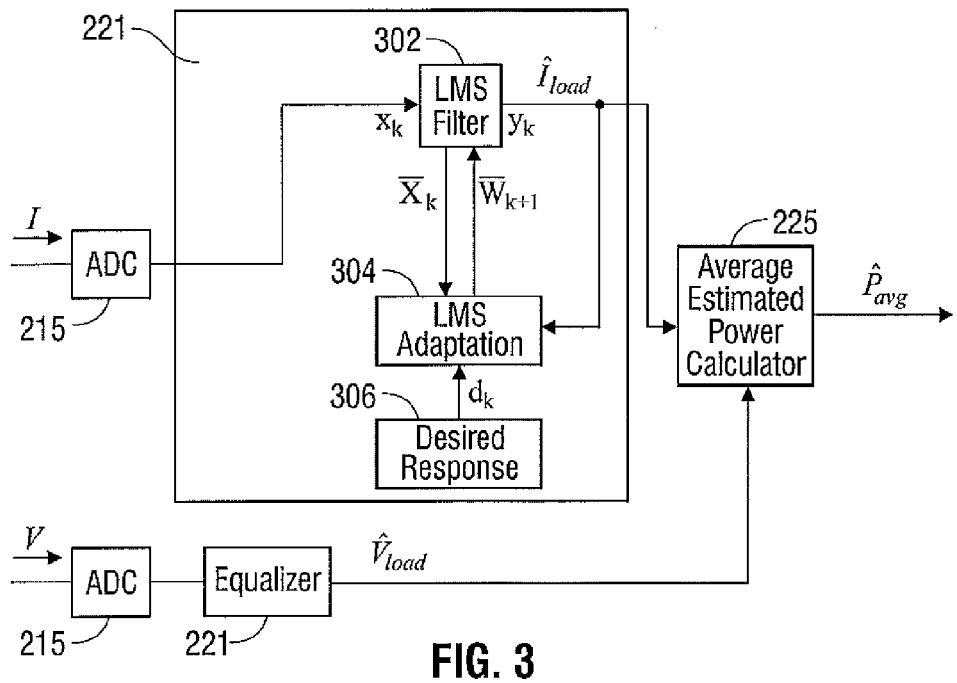
FIG. 3 is a block diagram of the equalizer of FIG. 2 in accordance with an embodiment of the present disclosure.

FIG. 3 is a block diagram of an equalizer 221 that uses a least means squares (LMS) finite impulse response (FIR) adaptive filter according to an embodiment of the present disclosure. The equalizer 221 includes an LMS filter 302, an LMS weight adaptation unit 304, a desired response input unit 306, and an average estimated power ($\hat{P}_{avg}$) calculator 308. The equalizer may be implemented using a polyphase structure, such as the polyphase structure shown in FIG. 6B. The LMS filter 302 filters a digital input value $x_k$ (e.g., a digital value representing the measured voltage or the measured current) based upon a weight vector $\overline{W}_{k+1}$ to produce a filtered output value $y_k$. The weight vector $\overline{W}_{k+1}$ is produced by the LMS weight adaptation unit 304 based upon the filtered output value $y_k$ and a desired response $d_k$.

The desired response $d_k$ for the LMS adaptation unit 304 may be a pre-computed "pseudo-filter," or time sequence. The desired response $d_k$ may have an idealized magnitude and phase versus frequency response of a converged adaptive filter in the electrosurgical system. For instance, if the converged output current from the system matches the pre-measured magnitude and phase values at one or more frequencies, then this information is used to construct a sequence $d_k$ and/or the pseudo-filter.

A desired response sequence $d_k$ may be constructed during a calibration process for the electrosurgical generator 102. For a single frequency $f_1$, the calibration process first involves using the RF Output Stage 204 to generate the following test signal:

$$x(t)=A_1 \sin(2\pi f_1 t),$$

where the amplitude $A_1$ is a measured or known value. The test signal is applied to a resistive load (e.g., the test resistor 910 of FIG. 9), which is chosen to provide minimal phase shift for a nominal voltage and current. The desired response unit 306 then generates a desired response sequence $d_k$.

The desired response sequence $d_k$ is formed by sampling a sinusoidal calibration signal $d(t)$ having a known amplitude of excitation or the same amplitude as the test signal $x(t)$ (i.e., $A_1$), but delayed according to a measured or known phase $\theta_1$ between the input of the ADCs 215 and the output $y_k$ of the adaptive filter (i.e., the combination of the LMS filter 302 and the LMS adaptation unit 304). In other words, the phase $\theta_1$ represents the delays introduced by the ADCs 215 and other electronic or digital components disposed between the RF Output Stage 204 and the output $y_k$ of the LMS filter 302. Such a calibration signal may be expressed as follows:

$$d(t)=A_1 \sin(2\pi f_1 t+\theta_1).$$

For multiple frequencies $f_n$, where n=1, ..., N, the calibration process involves using the RF Output Stage 204 to generate the following series of test signals:

$$x_n(t)=A_n \sin(2\pi f_n t),$$

where n=1, ..., N and the amplitudes $A_n$ are measured or known values. The series of test signals are summed together and applied to a resistive load (e.g., the test resistor 910 of FIG. 9).

The desired response sequence $d_k$ for multiple frequencies is formed by sampling the sum of multiple sinusoidal calibration signals given by the expression:

$$d_n(t)=A_n \sin(2\pi f_n t+\theta_n),$$

where n=1, ..., N. The calibration signals $d_n(t)$ have known amplitudes of excitation or the same amplitudes as the respective test signals $x_n(t)$ (i.e., $A_n$), but are delayed according to measured or known phases $\theta_n$ between the input of the ADCs 215 and the output $y_k$ of the adaptive filter (i.e., the combination of the LMS filter 302 and the LMS adaptation unit 304).

At the end of adaptation, the estimated phases or delays of the voltage and current will be equal to or approximately equal to each other at desired frequencies of interest, leaving only a difference between the measured phases or delays of the voltage current. Also, the magnitudes of the measured voltage and current will be identical to or approximately identical to the respective magnitudes of the estimated voltage and current.

Figure 4:
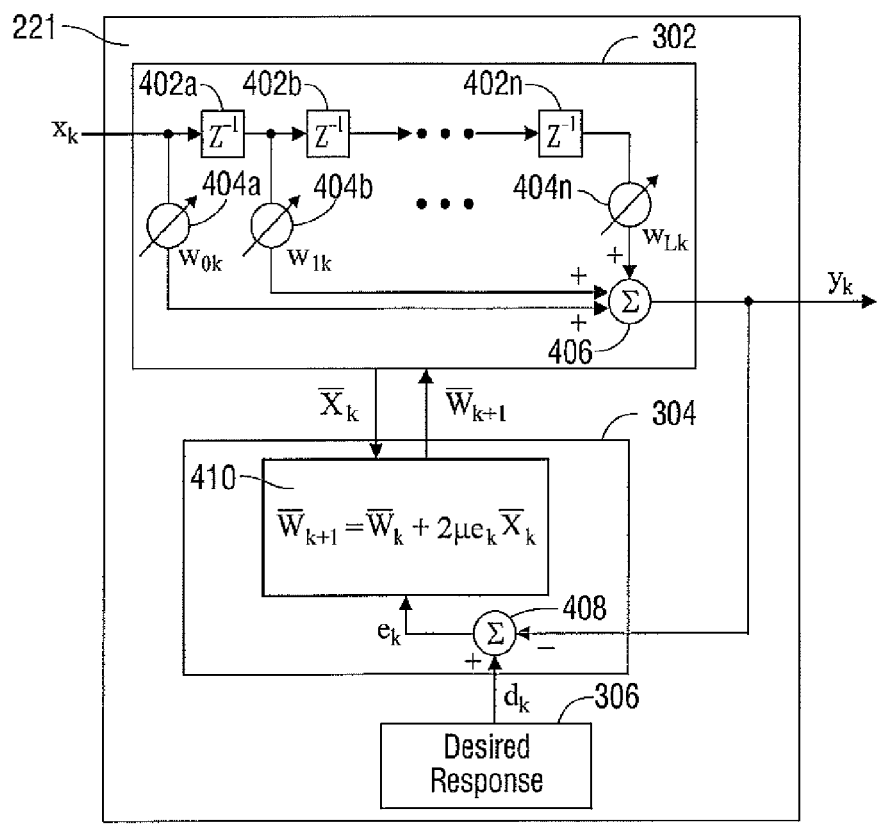
FIG. 4 is a block diagram of the equalizer of FIG. 2 in accordance with another embodiment of the present disclosure.

FIG. 4 is a detailed block diagram of an equalizer 221 that uses an LMS filter according to other embodiments of the present disclosure. The LMS filter 302, which may be a finite impulse response (FIR) filter, includes a series of time shifting units 402a-402n and a series of weighting units 404a-404n coupled to the digital input signal $x_k$. During operation, the updated weight vector $\overline{W}_{k+1}$ is fed from the LMS adaptation unit 304 to the LMS filter 302 and becomes the current weight vector $\overline{W}_k$, which includes weight values $w_{0k}$, $w_{1k}$, ..., $w_{Lk}$. The first weighting unit 404a multiplies the digital input signal $x_k$ by the first weight value $w_{0k}$ of the current weight vector $\overline{W}_k$. The time-shifting units 402b-n time shift the digital input signal $x_k$ to obtain time-shifted digital input signals $x_{k-1}, x_{k-2}, \ldots x_{k-L}$. The digital input signal $x_k$ and the time-shifted digital input signals $x_{k-1}, x_{k-1}, \ldots, x_{k-L}$ together form a digital input vector $\overline{X}_k$.

As shown in FIG. 4, the weighting units 404b-n are connected to respective outputs of the time-shifting units 402b-n. In this configuration, the weighting units 404b-n multiply the time-shifted digital input signals $x_{k-1}, x_{k-1}, \ldots x_{k-L}$ of the digital input vector $\overline{X}_k$ by respective weight values $w_{1k}, \ldots, w_{Lk}$ of the current weight vector $\overline{W}_k$. The results of time-shifting and weighting the digital input signal $x_k$ are added together by an adder 406 to obtain the digital output signal $y_k$.

The digital output signal $y_k$ is fed back to the LMS weight adaptation unit 304, in which the digital output signal $y_k$ is subtracted from the desired response $d_k$ by a subtractor 408 to obtain a digital error signal $e_k$. The LMS weight adaptation unit 304 includes an update computation unit 410 that uses the digital error signal $e_k$, the input vector $\overline{X}_k$, and the weight vector $\overline{W}_k$ to compute an updated weight vector $\overline{W}_{k+1}$ according to the following LMS update equation:

$$\overline{W}_{k+1}=\overline{W}_k+2\mu e_k \overline{X}_k,$$

where $\mu$ is chosen by the designer and is bounded by:

$$0 < \mu < \frac{1}{(L+1)(\text{Signal Power of } \overline{X}_k)}.$$

The advantage of an equalizer 221 using the LMS filter 302 is that it can accurately equalize the voltage and current measurements at all frequencies of interest. The LMS filter may be trained when the generator is calibrated. The LMS filter 302 may also be trained periodically throughout the life of the electrosurgical generator 102. In some embodiments, once the LMS filter 302 is trained, the LMS weight adaptation unit 304 does not adapt the weight vector $W_{k+1}$, but keeps it fixed.

Figure 5:
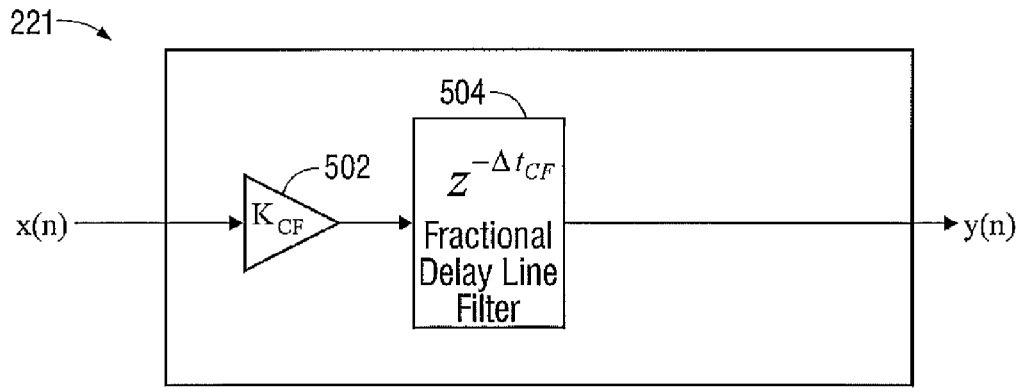
FIG. 5 is a block diagram of the equalizer of FIG. 2 that includes a fractional delay line filter block in accordance with another embodiment of the present disclosure.

FIG. 5 is an equalizer 221 according to another embodiment of the present disclosure. The equalizer 221 compensates for the gain and "phase" (in terms of delay) at a single frequency. The equalizer 221 includes a gain unit 502 and a fractional delay line 504. The gain unit 502 amplifies an input signal x(n) according to a gain correction factor $K_{CF}$, which is determined from a calibration procedure described below. During the calibration procedure, the gain correction factor $K_{CF}$ is adjusted until the magnitude of the signal output from block 504 matches a test signal (e.g., a measured or known reference signal) input to the voltage sensor 211 and the current sensor 212 of FIG. 2. This is similar to the results of the LMS adaptation at a single frequency described above.

The amplified input signal is then applied to the fractional delay line 504, which may be expressed as $z^{-\Delta t_{CF}}$, where $\Delta t_{CF}$ is the time-delay correction factor. The time-delay correction factor $\Delta t_{CF}$ may be determined through a calibration procedure where the nominal phase or delay differences through the voltage sensor 211 and the current sensor 212 are matched or made equal to a measured or known reference value. The fractional delay line 504 may combine an interpolation stage with a decimation stage to arrive at fractional sample delay times. The fractional delay line 504 feeds an output signal y(n) to the average estimated power calculator 225 of FIG. 2.

Figure 9:
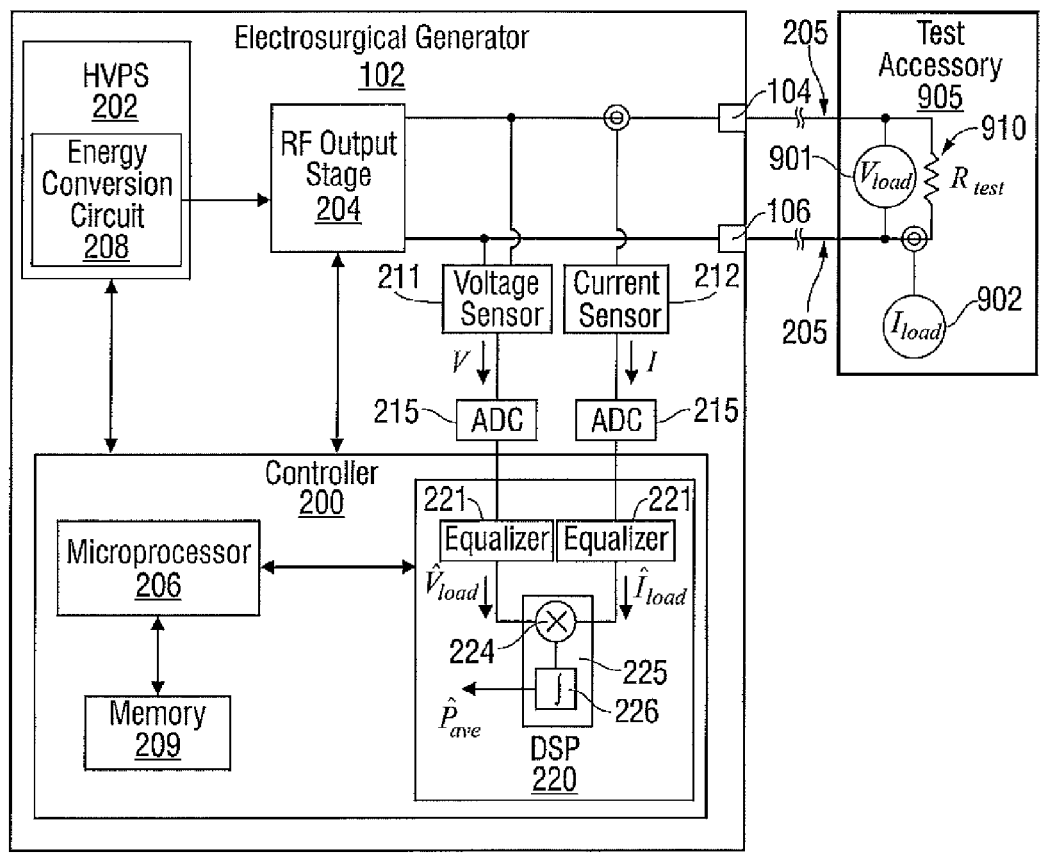
FIG. 9 is a block diagram of the electrosurgical generator of FIG. 1 coupled to a test accessory in accordance with embodiments of the present disclosure.

The calibration procedure for determining the gain correction factor $K_{CF}$ may involve using a test accessory 905 together with the electrosurgical generator 102 of FIG. 2, as illustrated in the block diagram FIG. 9. The test accessory 905 includes a test resistance 910 ($R_{test}$) that represents a load, a voltage reference meter 901 for measuring the voltage across the test resistance 910, and a current reference meter 902 for measuring the current passing through the test resistance 910. The test accessory 905 may include connectors that allow the test accessory 905 to be removed from or connected to the terminals 104, 106 of the electrosurgical generator 102. In other embodiments, the test accessory 905 may be integrated into the electrosurgical generator 102.

The test accessory 905 is used to calibrate the sensors 211, 212 and equalizers 221, 222 for magnitude and phase at one or more frequencies. The calibration process first involves applying the test resistance $R_{test}$ of the test accessory 905 across the output terminals 104, 106. The value of the test resistance $R_{test}$ is selected to provide minimal phase shift for a nominal voltage and current. Then, the RF Output Stage 204 generates one or more test signals at desired frequencies $\omega_d$. Next, a reference voltage magnitude $\|v\|$ and a phase angle $\phi_v$ are measured at each of the desired frequencies $\omega_d$ using the voltage reference meter 201. Also, a reference current magnitude $\|i\|$ and phase angle $\phi_i$ are measured at each of the desired frequencies $\omega_d$ using the current reference meter 202. At the same time, the voltage sensor 211, the current sensor 212, the ADCs 215, and the equalizers 221 produce an estimated voltage magnitude $\|\hat{v}\|$ and phase angle $\hat{\phi}_v$ and an estimated current magnitude $\|\hat{i}\|$ and phase angle $\hat{\phi}_i$ at each of the desired frequencies $\omega_d$ of the test signals.

For each desired frequency $\omega_d$, the gain correction factors for the voltage and current equalizers $K_{EQ\_V}(\omega_d)$ and $K_{EQ\_I}(\omega_d)$ are calculated according to the following equations:

$$K_{EQ\_V}(\omega_d) = \frac{\|\hat{v}\|}{\|v\|}(\omega_d) \text{ and } K_{EQ\_I}(\omega_d) = \frac{\|\hat{i}\|}{\|i\|}(\omega_d).$$

Then, for each desired frequency $\omega_d$, the minimum phases of the equalizers $\phi_{EQ\_V}(\omega_d)$ and $\phi_{EQ\_I}(\omega_d)$ are determined such that $\hat{\phi}_v = \phi_i$ and $\phi_v - \hat{\phi}_i = \hat{\phi}_v - \hat{\phi}_i$. It is desirable to achieve "minimum" phase or delay because the voltage and current measurements are in a closed loop and excessive phase or delay reduces the phase margin or bandwidth of the closed loop.

Figure 10:
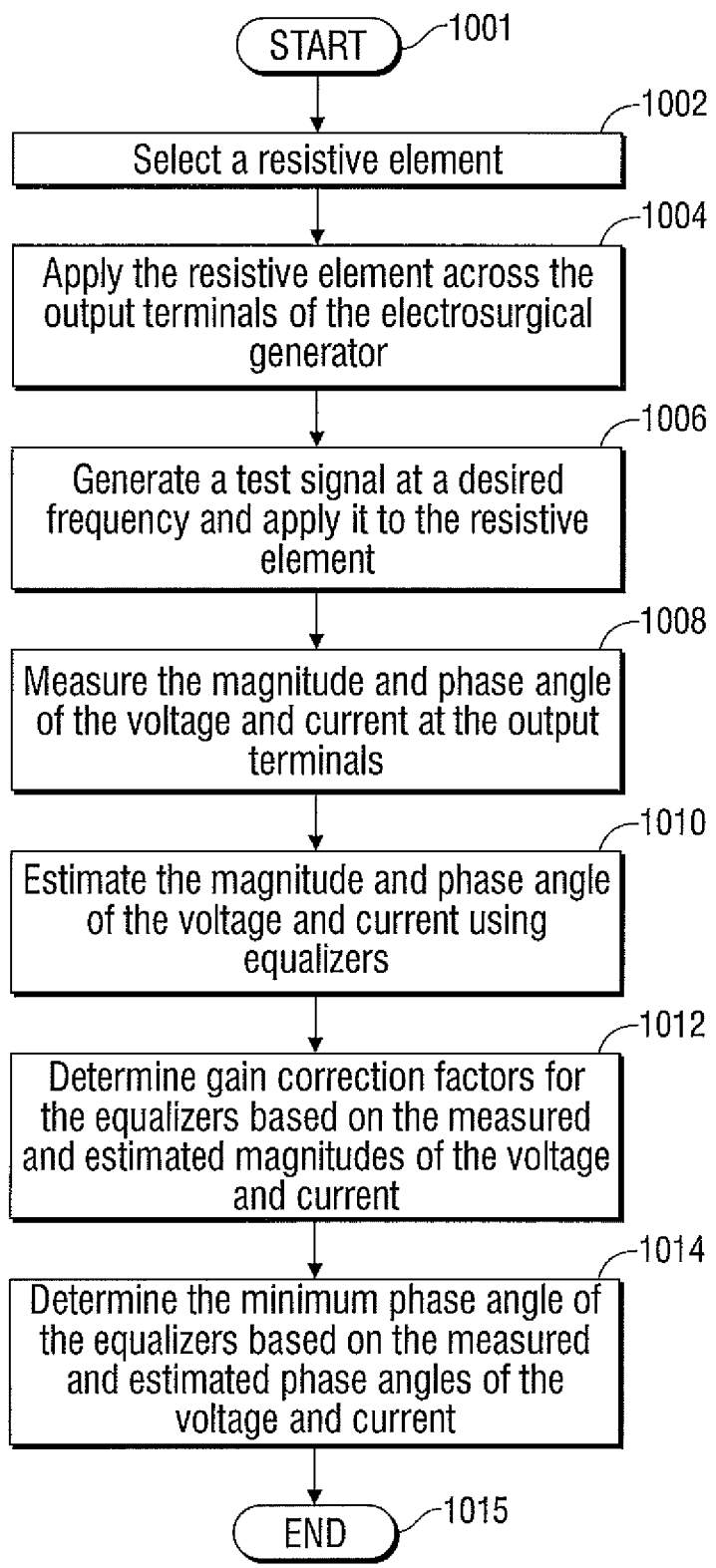
FIG. 10 is a flow diagram of a method of calibrating power measurements in an electrosurgical generator in accordance with other embodiments of the present disclosure.

FIG. 10 is a flow diagram of a general method of calibrating an electrosurgical generator according to embodiments of the present disclosure. After starting in step 1001, a resistive element having appropriate characteristics is selected in step 1002. In step 1004, the resistive element is applied across the output terminals of the electrosurgical generator. In step 1006, a test signal is generated at a desired frequency, and, in step 1008, the test signal is applied to the resistive element.

In step 1008, first magnitude values and first phase angle values of voltage and current components of the test signal are measured at the output terminals. In step 1010, second magnitude values and second phase angle values for the voltage and current components of the test signal are estimated using a first equalizer for the voltage component (e.g., the equalizer 221 of FIG. 2) and a second equalizer for the current component (e.g., the equalizer 221 of FIG. 2). In step 1012, gain correction factors, e.g., $K_{EQ\_V}(\omega_d)$ and $K_{EQ\_I}(\omega_d)$, for the first and second equalizers are determined based upon the measured and estimated magnitudes of the voltage and current components of the test signal. Finally, before the calibration process ends (step 1015), the minimum phase angle for the first and second equalizers is determined in step 1014 based on the measured and estimated phase angles of the voltage and current components of the test signal obtained in steps 1008 and 1010. The minimum phase angle information may be used to determine the time-delay correction factor $\Delta t_{CF}$.

Figure 6A:
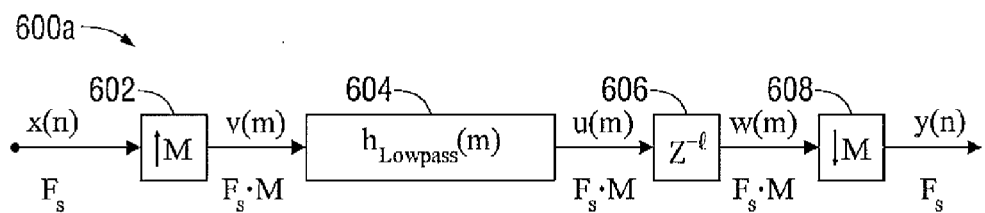
FIGS. 6A and 6B are block diagrams of the fractional delay line block of FIG. 5 in accordance with embodiments of the present disclosure.

The fractional delay line 504 of FIG. 5 may be implemented with a multi-rate structure. FIG. 6A is a diagram of a multi-rate structure 600a for obtaining a fractional fixed delay of l/M samples. The input signal x(n), which has been sampled at the sample frequency $F_s$, is applied to an interpolator 602. The interpolator 602 up-samples the input signal x(n) by a factor of M($F_s \cdot L$) to obtain an up-sampled or interpolated signal v(m). The up-sampled signal v(m) is then filtered by a digital lowpass filter 604 to remove the images (i.e., the extra copies of the basic spectrum) created by the interpolator 602. The resulting filtered signal u(m) is then delayed by l samples by a delay unit 606. Finally, the output w(n) from the delay unit 606 is down-sampled by a factor of M by the decimator 608 to obtain an equalized output signal y(n) at the original sample frequency $F_s$.

Figure 6B:
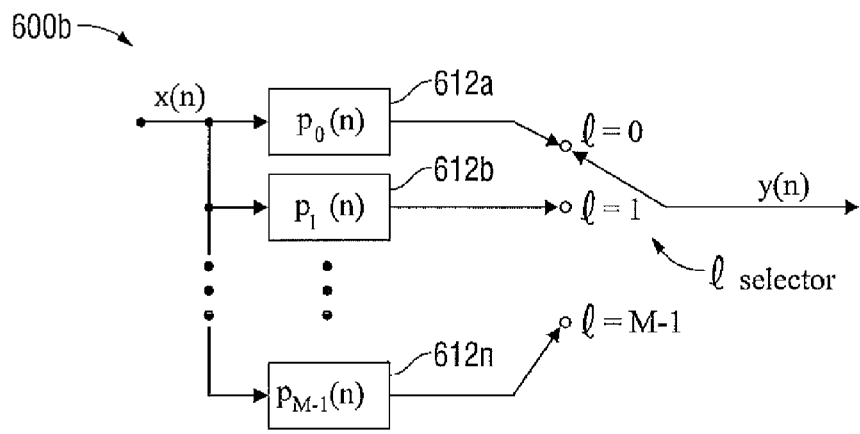

FIG. 6B is a diagram of an efficient polyphase implementation 600b of the multi-rate structure of FIG. 6A. This implementation includes a series of transversal FIR filters 612a-612n that filter the input signal x(n). The transversal FIR filters 612a-612n are given by the following difference equation:

$$p_r(n) = h_{Lowpass}(nM+r), 0 \le r \le (M-1).$$

The delay of l is implemented as the initial position of the commutator switch ("l selector") 614 corresponding to the sample at n=0.

Figure 7A:
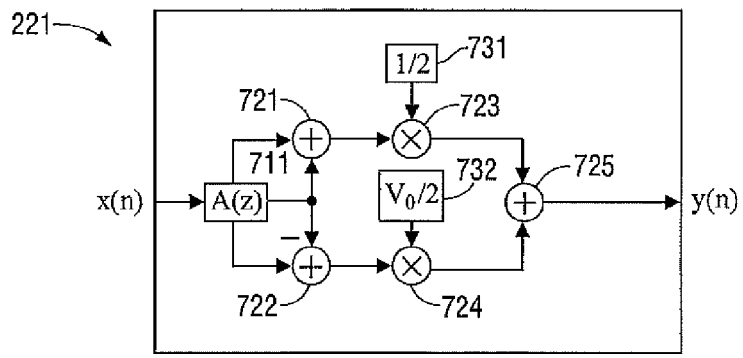
FIGS. 7A-7C are block diagrams of equalizers in accordance with other embodiments of the present disclosure.
Figure 7B:
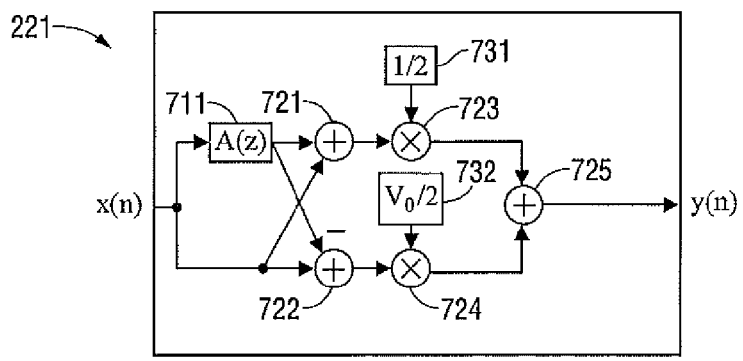
Figure 7C:
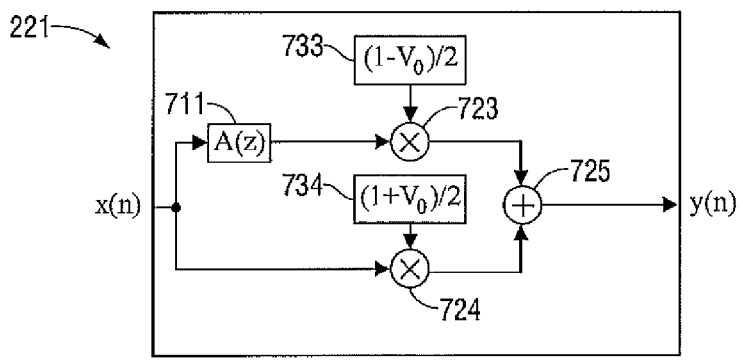

FIGS. 7A-7C are diagrams of equalizers 221 that combine a simple gain with an "all-pass" delay filter. The all-pass delay may be either a first-order or second-order all-pass filter. The all-pass filter may be better at modeling the group delay across a relatively narrow bandwidth of interest than a simple gain combined with a fractional delay, which may be good at a single frequency, but may not be better than the LMS adaptive filter in magnitude and phase across a broad band of frequencies.

In the Laplacian s-domain, a first-order all-pass filter, which may be used to change delay or phase but not magnitude, is represented by the following transfer function:

$$A(s) = \frac{s - \alpha_0}{s + \alpha_0}.$$

The magnitude of the first-order all-pass transfer function is:

$$|A(s)| = |H(s)| = \frac{|s - \alpha_0|}{|s + \alpha_0|} = \frac{\sqrt{\alpha_0^2 + \omega_c^2}}{\sqrt{\alpha_0^2 + \omega_c^2}} = 1$$

and the phase (in radians) is:

$$\beta(\omega_c) = -2\tan^{-1}\left(\frac{\omega_c}{\alpha_0}\right),$$

where the phase angle is 0 degrees when $\omega_c=0$, −90 degrees when $\omega_c=\alpha_0$, and −180 degrees when $\omega_c \gg \alpha_0$. By fixing $\omega_c$, the phase $\beta(\omega_c)$ is set by $\alpha_0$. The group delay of the first-order all-pass transfer function is given by:

$$T_{gd} = \frac{2\alpha_0}{\alpha_0^2 + \omega_c^2}.$$

The first-order all-pass filter is implemented in the digital domain. There are many ways to implement the first-order all-pass filter. One method is to apply the bilinear transform by replacing the Laplacian variable s with $$\frac{2}{T}\left(\frac{1-z^{-1}}{1+z^{-1}}\right),$$

where T is the sample period. Then, the digital all-pass transfer function becomes $$H(z) = \frac{1 - k_1 z^{-1}}{k_1 - z^{-1}},$$

where $$k_1 = \frac{1 + \frac{T}{2}\alpha_0}{1 - \frac{T}{2}\alpha_0}.$$

This digital all-pass transfer function may be implemented by the following difference equation:

$$y(n) = \frac{1}{k_1} \cdot x(n) - k_1 \cdot x(n-1) + \frac{1}{k_1} \cdot y(n-1)$$

Another method to implement a first-order all-pass filter is to use a simple feedforward/feedback digital comb filter having the following transfer function:

$$H(z) = \frac{a - z^{-M}}{1 + a \cdot z^{-M}},$$

where a is a constant and M is an arbitrary integer delay and M≥0. This transfer function may be implemented by the following difference equation:

$$y(n) = a \cdot x(n) + x(n-M) - a \cdot y(n-M).$$

Figure 8:
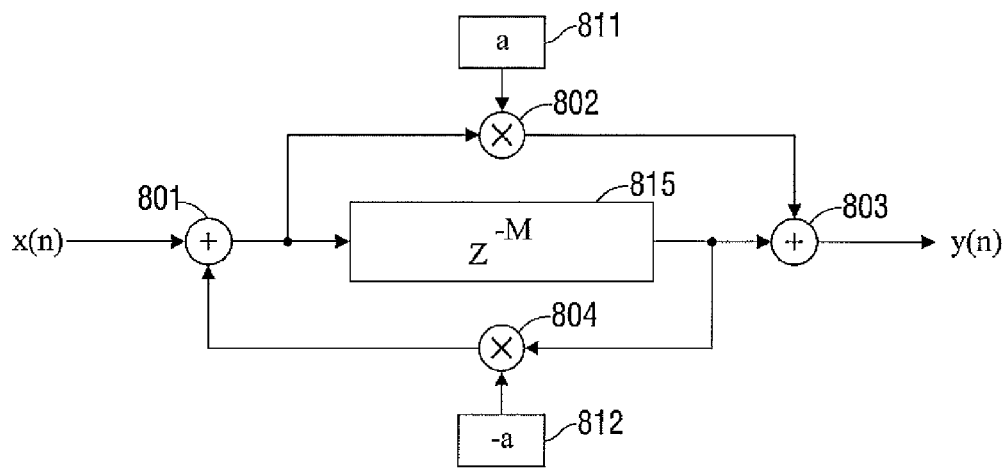
FIG. 8 is a block diagram of an equalizer in the form of a digital comb filter in accordance with other embodiments of the present disclosure.

FIG. 8 shows a digital circuit that implements the feedforward/feedback digital comb filter. The digital circuit includes first and second adders 801, 803, first and second multipliers 802, 804, constant blocks 811, 812, and a delay block 815, which provides a delay of M samples. The second multiplier 804 multiplies the output of the delay block 815 by a constant −a. The first adder 801 adds the output from the second multiplier 804 to the input x(n) and provides the result to the delay block 815. The first multiplier 802 multiplies the output from the first adder 801 by a constant a. The second adder 802 adds the output of the first multiplier 802 to the output of the delay block 815 to produce the output y(n).

Another type of filter that combines an all-pass delay with a gain is a shelving filter. The shelving filter can be used to perform weighting of certain frequencies while passing other frequencies. The shelving filter can be useful in emphasizing the signal band of interest. A first-order parametric shelving filter transfer function is given by $$H(s) = \frac{1}{2}[1 + A(s)] + \frac{V_0}{2}[1 - A(s)],$$

where A(s) is the first-order all-pass transfer function described above.

To implement a digital shelving filter, the first-order transfer function H(s), which is in the s-domain, is converted to the z-domain. The transfer function H(s) may be converted to the z-domain using the bilinear transform to obtain the following transfer function:

$$H(z) = \frac{1}{2}[1 + A(z)] + \frac{V_0}{2}[1 - A(z)],$$

where $$A(z) = \frac{-(a + z^{-1})}{1 + az^{-1}},$$

$$a = \frac{\tan\left(\frac{\omega_c T}{2}\right) - V_0}{\tan\left(\frac{\omega_c T}{2}\right) + V_0}$$

for a frequency response that provides a cut, and $$a = \frac{\tan\left(\frac{\omega_c T}{2}\right) - 1}{\tan\left(\frac{\omega_c T}{2}\right) + 1}$$

for a frequency response that provides a boost.

The frequency response of the transfer function that provides a cut attenuates a range of frequencies and passes (i.e., applies a gain of 1 to) an adjacent range of frequencies. On the other hand, the frequency response of the transfer function that provides a boost amplifies a range of frequencies and passes an adjacent range of frequencies. The response of the shelving filter may be modified by independently controlling the cutoff/center frequency $\omega_c$ and the gain $V_0$.

The shelving filter transfer function H(z) may be implemented with the equalizer structures shown in FIGS. 7A-7C. As shown in FIG. 7A, the equalizer 221 includes an all-pass delay filter 711 ("A(z)"), an adder 721, and a subtractor 722. The all-pass delay filter 711 filters the input signal x(n) to obtain a filtered signal. The all-pass delay filter A(z) 711 may be implemented as a difference equation that is computed with a digital signal processor. The adder 721 adds the filtered signal to the input signal x(n) and the subtractor 722 subtracts the filtered signal from the input signal x(n).

The equalizer 221 of FIG. 7A also includes a first multiplier 723, a second multiplier 724, and an adder 725 coupled together. The first multiplier 723 multiplies the output from the adder 721 by a first gain 731 of 0.5 (or a 1-bit shift to the right) and the second multiplier 724 multiplies the output from the subtractor 722 by a second gain 732 of $V_0/2$, where $V_0$ is the gain of the all-pass filter when the frequency is zero. Finally, the adder 725 adds the outputs from the first multiplier 723 and the second multiplier 724 to obtain the output signal y(n).

FIG. 7B is an equalizer 221 according to another embodiment of the present disclosure. The equalizer 221 of FIG. 7B includes the same components and connections as the equalizer 221 of FIG. 7A except that the components and connections of the equalizer 221 of FIG. 7B are arranged differently. FIG. 7C is an equalizer 221 according to yet another embodiment of the present disclosure. The input signal x(n) is filtered by the all-pass delay filter 711 and then multiplied by the gain $(1-V_0)/2$ (733) using the first multiplier 723. The input signal x(n) is multiplied by the gain $(1+V_0)/2$ (734) using the second multiplier 724. Then, the adder 725 adds the results of the first and second multipliers together to obtain an equalized output signal y(n).

Another embodiment of the equalizer 221 may use a peak filter to boost or cut any desired frequency. A second-order peak filter may be implemented with the equalizers 221 of FIGS. 7A-7C, where the all-pass transfer function in the Z-domain is given by:

$$A(z) = \frac{z^{-2} + d(1 + a_{BC})z^{-1} + a_{BC}}{1 + d(1 + a_{BC})z^{-1} + a_{BC}z^{-2}},$$

where $d = -\cos(\Omega_C)$, $V_0 = H(e^{\Omega_C})$, $$a_B = \frac{1 - \tan\left(\frac{\omega_b T}{2}\right)}{1 + \tan\left(\frac{\omega_b T}{2}\right)}, \text{ and } a_C = \frac{V_0 - \tan\left(\frac{\omega_b T}{2}\right)}{V_0 + \tan\left(\frac{\omega_b T}{2}\right)}.$$

The center frequency $f_c$ of the peak filter is determined by the parameter d, the bandwidth $f_b$ is determined by the parameters $a_B$ and $a_C$, and the gain is determined by the parameter $V_0$.

Using the equalizers 221 of FIGS. 7A-7C, power measurements may be calibrated in a manner similar to the examples described above by first determining the desired gain and phase. The desired gain is determined based upon the difference between the measured ratio of gains and an ideal or reference ratio of gains and the desired phase is determined based upon the difference between the measured phase and an ideal or reference phase. Then, it is determined whether the gain represents a cut (e.g., $V_0<0$) or a boost (e.g., $V_0>0$). Finally, the digital all-pass transfer function A(z) having appropriate parameters is substituted into the equalizers 221 of FIGS. 7A-7C.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An electrosurgical generator system, comprising:
    an electrosurgical generator including:
        an electrical energy source;
        a voltage detector coupled to the electrical energy source and configured to detect a voltage;
        a current detector coupled to the electrical energy source and configured to detect a current;
        an equalizer configured to estimate voltage and current applied to a load based on the detected voltage and current; and
        a power calculation unit configured to calculate power applied to the load based on the estimated voltage and current; and
    an electrosurgical instrument coupled to the electrosurgical generator through an electrosurgical cable, the electrosurgical instrument configured to apply electrosurgical energy to tissue,
    wherein the equalizer includes a gain element and a fractional delay line filter configured to minimize a phase difference between the estimated voltage and current, and
    wherein the fractional delay line filter includes an interpolation stage and a decimation stage to obtain fractional sample delay times.

2. The electrosurgical generator system according to claim 1, wherein the equalizer includes a polyphase filter and a decimator.

3. The electrosurgical generator system according to claim 1, wherein the power calculation unit calculates actual power applied to the load.

4. The electrosurgical generator system according to claim 1, further comprising analog-to-digital converters electrically coupled to the current and voltage detectors.

5. The electrosurgical generator system according to claim 1, wherein the electrosurgical generator includes a digital signal processor, which includes the equalizer and the power calculation unit.

6. The electrosurgical generator system according to claim 1, wherein the equalizer includes:
    a voltage equalizer configured to estimate a voltage applied to the tissue; and
    a current equalizer configured to estimate a current applied to the tissue.

* * * * *